United States Patent [19]

Persson

[11] 4,116,548
[45] Sep. 26, 1978

[54] ADJUSTABLE SUPPORT
[75] Inventor: Staffan B. Persson, Kenmore, N.Y.
[73] Assignee: American Optical Corporation, Southbridge, Mass.
[21] Appl. No.: 773,572
[22] Filed: Mar. 2, 1977
[51] Int. Cl.² .............................................. A61B 3/00
[52] U.S. Cl. .................................... 351/38; 248/419; 248/421
[58] Field of Search .................... 351/38; 248/23, 419, 248/421

[56] References Cited
U.S. PATENT DOCUMENTS
3,075,736  1/1963  Freedman .......................... 248/419 X
3,475,075  10/1969  Stone, Jr. ............................ 351/38 X Primary Examiner—Paul A. Sacher
Attorney, Agent, or Firm—Jeremiah J. Duggan; Alan H. Spencer

[57] ABSTRACT

A mechanism for supporting an instrument which provides finger-tip adjustment in two or three directions is described. Torsional springs are used to counterbalance the instrument weight. An interconnected linkage arrangement permits vertical motion and horizontal motion in one direction. Horizontal motion in the other direction is obtained by axially sliding the instrument frame along shafts extending between pivot points of the interconnected linkage.

An optional feature for ophthalmic instruments includes a mechanism for alternatively shifting the instrument in a horizontal direction between first and second chosen positions.

10 Claims, 7 Drawing Figures

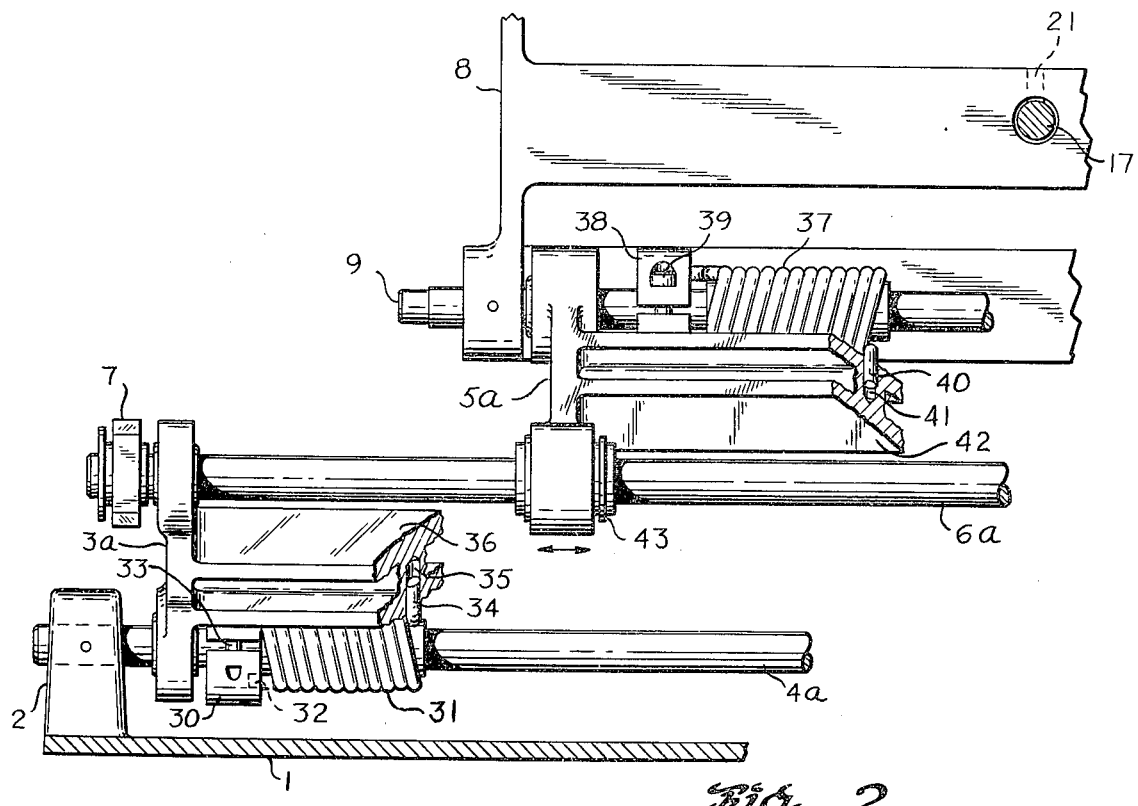
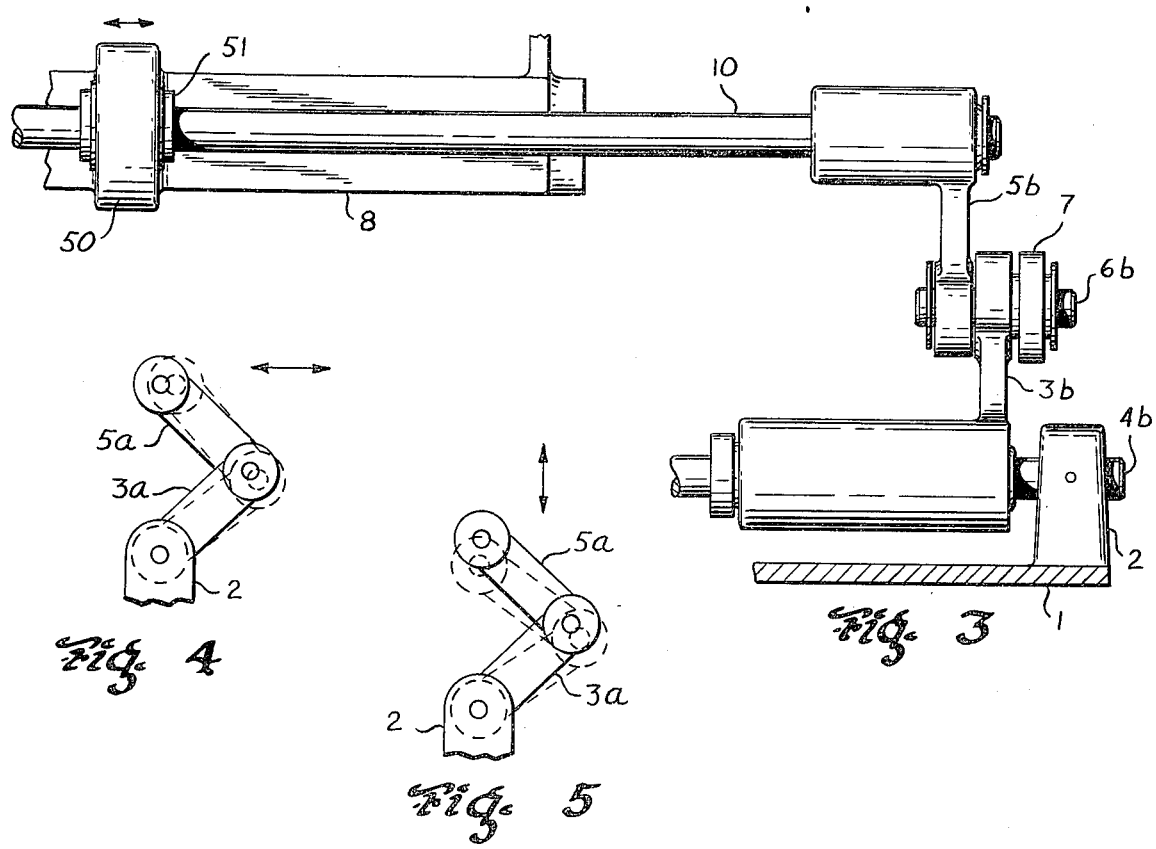

ADJUSTABLE SUPPORT

BACKGROUND OF THE INVENTION

This invention relates to mechanisms for supporting ophthalmic instruments and more particularly to such mechanisms permitting adjustment of the instrument in two or three directions.

Ophthalmic instruments, such as slit lamps, non contact tonometers, objective refractors and subjective refractors require precise alignment of the instrument optical axis with the optical axis of the eye. The optics, mountings therefor and mechanisms associated therewith may weigh as much as 50 lbs. Such devices, because of the precision of alignment required, have usually been constructed with a base providing bidirectional horizontal motion that may be controlled with a single lever or a joy-stick. Such mechanisms provide finger-tip control in the horizontal motion. However, vertical control is usually obtained by rotating a screw to adjust the height of the instrument. A separate control is required for elevation and the construction of such units greatly increases the total weight of the unit.

It is an object of the present invention to provide improved finger-tip adjustment of elevation and at least one horizontal direction.

It is a further object of the present invention to provide a single lever control for three-directional motion.

It is a still further object of the present invention to provide a light-weight supporting mechanism for ophthalmic instruments which permits accurate alignment with little effort on the part of the practitioner.

BRIEF DESCRIPTION OF THE PRESENT INVENTION AND DRAWINGS

A plurality of interconnected upper and lower links pivotably attached to a base at one end and pivotally connected to an instrument frame at the other end provides vertical adjustment by varying the angle between the links and substantially horizontal adjustment in one direction by rotation of the interconnected links without change in the angle therebetween. Torsional means, preferably coil springs, are used to counterbalance the instrument weight. By joining the pivot points interconnecting upper and lower links, parallelinity of the instrument frame and base is maintained.

FIG. 2 is an end view of the left half of the rear linkage assembly;

FIG. 3 is an end view of the right half of the front linkage assembly;

FIG. 4 is a schematic diagram of the linkage motion during front-back adjustment;

FIG. 5 is a schematic diagram of the linkage motion during vertical adjustment;

DETAILED DESCRIPTION OF THE INVENTION

Figure 1:
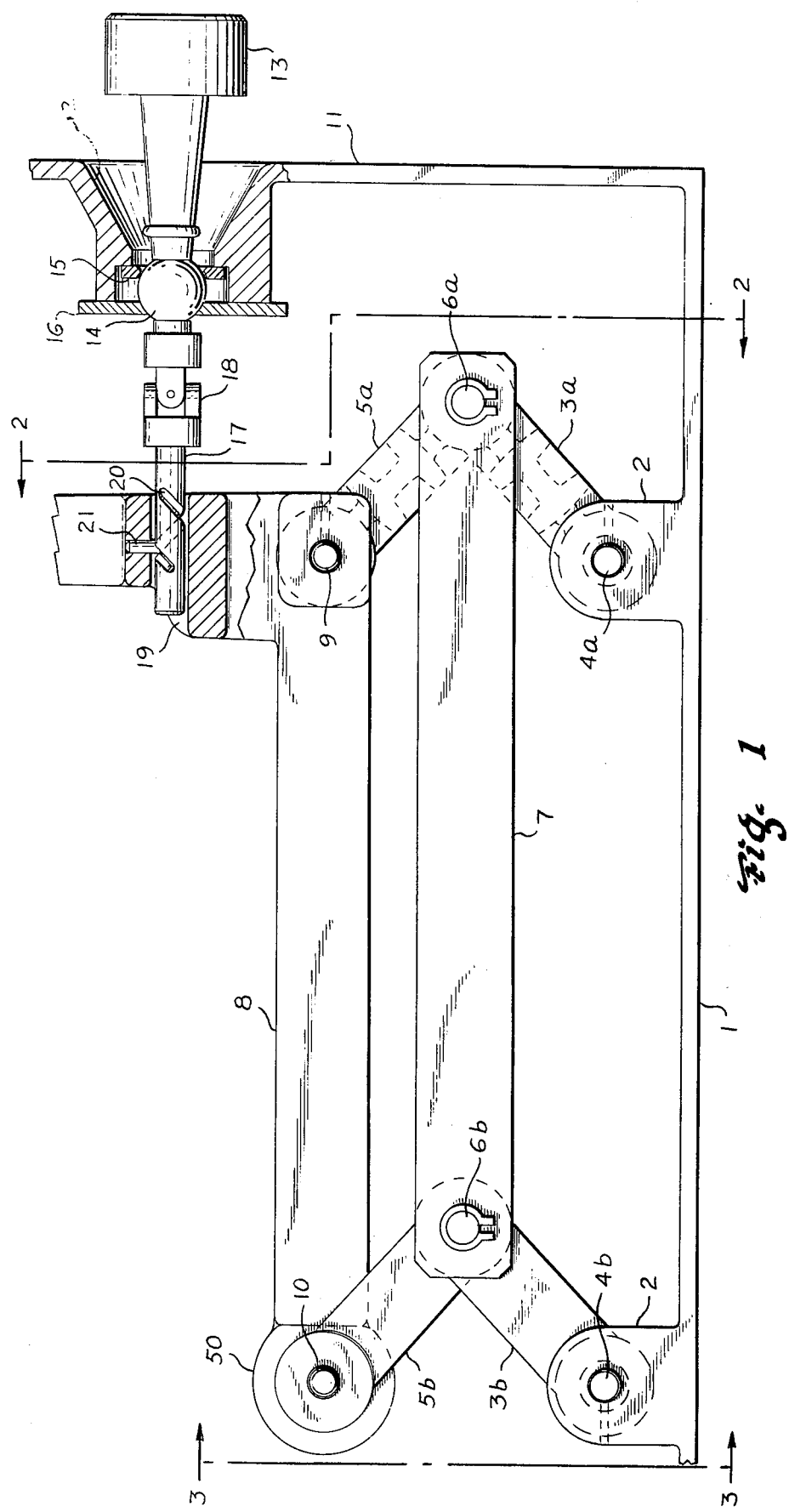
FIG. 1 is a side view of the linkage assembly.

Referring to FIG. 1, a base 1 (or support) has four upwardly extending ears 2 (two shown). Lower links 3a and 3b are pivotably connected at one end to ears 2 by shafts 4a and 4b. The other end of lower links 3a and 3b are pivotably connected to one end of upper links 5a and 5b by intermediate shafts 6a and 6b. A rigid member 7 extends between intermediate shafts 6a and 6b to maintain parallelinity between the rear linkage 3a, 4a and the front linkage 3b, 4b. The other end of upper links 5a and 5b are pivotably connected to instrument frame 8 by rear shaft 9 and front shaft 10. Case back 11 extends upwardly from base 1 and has a conical recess 12. Control 13 is mounted to move universally within recess 12 by ball 14 which is pivotably mounted between bushing 15 and cover 16. Control 13 is connected to shaft 17 by universal 18. Shaft 17 extends through bore 19 in instrument frame 8. A spiral groove 20 in shaft 17 engages follower 21 carried by instrument frame 8. Thus, rotation of the shaft in one direction increases the distance between the instrument frame 8 and case back 11 while rotation of the shaft in the other direction reduces the distance therebetween. This motion is exemplified in FIG. 4 and provides substantially horizontal adjustment in one direction when the angle between the lower links and the upper links remains constant. Moving control 13 in a vertical direction will provide a corresponding movement in the opposite direction of instrument frame 8. This vertical movement is accomplished by varying the angle between the lower links and the upper links as shown in FIG. 5.

Details of the counterbalancing means of the support system are shown in FIG. 2. Clamp ring 30 receives one end of coil spring 31 in hole 32. Screw 33 locks clamp ring 30 to shaft 4a. The other end 34 of coil spring 31 is positioned in hole 35 of bar 36 which joins left lower link 3a to its corresponding right link (not shown). Similarly, coil spring 37 is locked to shaft 9 by clamp ring 38 and screw 39. The other end 40 of coil spring 37 is positioned in hole 41 of crossbar 42. Crossbar 42 connects upper left rear link 5a to its corresponding right rear link (not shown). The crossbars 36 and 42 provide lateral, i.e. right and left, rigidity for maintaining parallelinity of the instrument frame 8 with base 1. Bearing 43 permits link 5a to axially slide along shaft 6a. Similarly, a bearing in the corresponding right rear link permits that link to axially slide with link 5a along shaft 6a. Preferably, coil springs 31 and 37 provide about equal contributions to supporting the instrument. From the drawing, it is clear that the lower coil spring 31 urges lower link 3a upwardly, while upper coil spring 37 urges upper link 5a downwardly. Coil springs 31 and 37 are adjusted to preload the desired amount of torque to their respective linkages by rotation of clamps 30 and 38. The clamps are then locked to their respective shafts 4a and 9.

The manner of connecting the front of instrument frame 8 to shaft 10 is shown in FIG. 3. A centrally-located protrusion 50 extends forward from instrument frame 8. Bearing 51 is carried by protrusion 50 and permits instrument frame 8 to move axially along shaft 10. When the instrument is an ophthalmic instrument, a mechanism for providing alternate positions is desirable. One such mechanism is shown in FIGS. 6 and 7.

Figure 6:
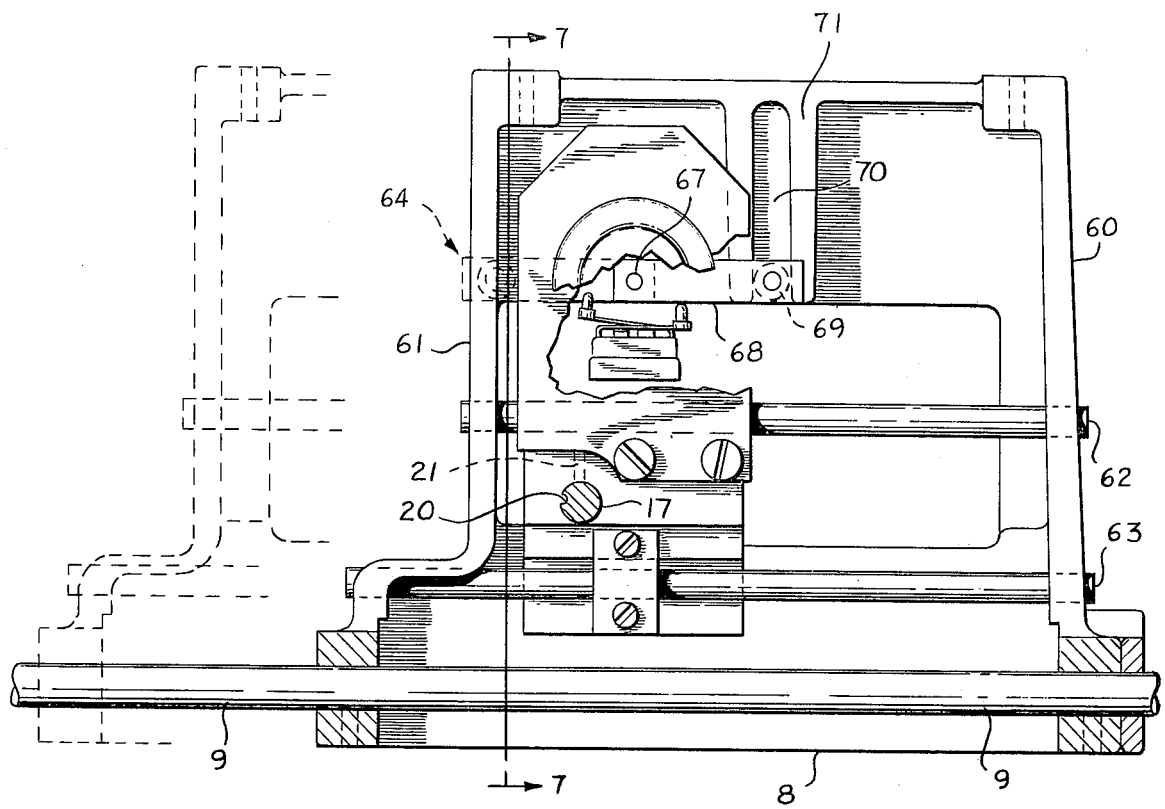
FIG. 6 is a back view, partly in section, of an optional embodiment for providing alternative instrument positioning.
Figure 7:
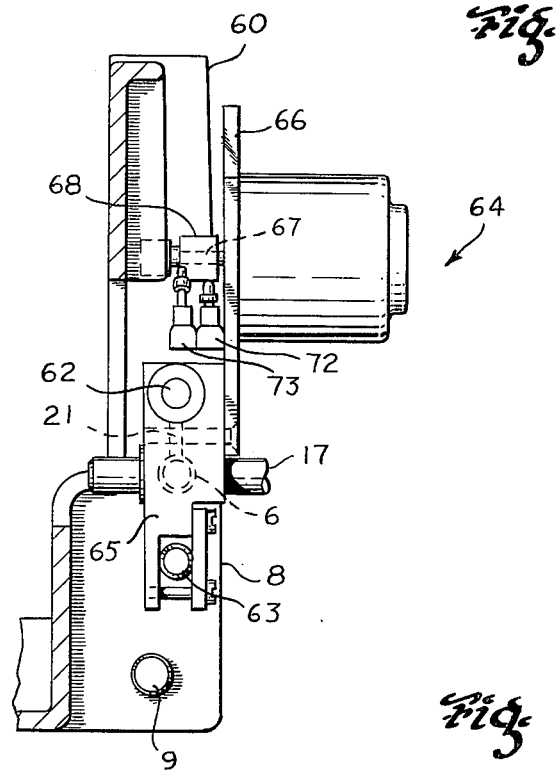
FIG. 7 is an end view, partly in section, of the optional embodiment of FIG. 6.

Referring to FIGS. 6 and 7, the instrument frame 8 has a pair of upwardly-extending side members 60 and 61. Upper rod 62 and lower rod 63 extend between side members 60 and 61 and are secured thereto. Shift mechanism 64 has a bore to receive control shaft 17 with groove 20 in body 65. Thus, movement of the finger-tip control 13 for vertical and forward-backward motion of the instrument is transmitted from the control through shaft 17 to body 65 thence through shafts 62, 63 to side members 60 and 61. Lateral motion is transmitted from shaft 17 to body 65 and thence through motor mount plate 66 to motor shaft 67. Arm 68 is mounted on motor shaft 67 and positions instrument frame 8 to the left or right of the motor shaft. As shown in FIG. 6, the instrument frame lies to the right of motor shaft 67 and is located by bearing 69 which is positioned in elongated recess 70 formed in frame back 71. A control switch (not shown) is wired through limit switches 72 and 73. Upon activation of the control switch, the motor would rotate shaft 67 in a counterclockwise direction through the closed circuit of limit switch 73. After rotation through an arc of 180°, arm 68 will close limit switch 73 stopping rotation of the arm. In this position, the circuit, including limit switch 72, is now open. When arm 68 extends to the left, as shown in dotted outline, the instrument frame will be moved approximately 65mm to the position partly shown by a dotted outline.

What is claimed is:

1. Apparatus for providing adjustment from a normal vertical position and a normal horizontal position of a device which comprises:

a support member, a plurality of interconnected first and second link members, each of said first and second links having a pair of parallel pivot axes, one pivot axis of each first link and one pivot axis of the interconnected second link being a common pivot axis interconnecting said first and second links, each of said second links being connected to said support at the other second link pivot axis, a frame member for supporting said device pivotably connected to each of said first links at the other first link pivot axis, a rigid member connecting each said common pivot axis for maintaining parallelinity between said support member and said frame member, torsion means connected to a link for substantially counterbalancing said device at said normal vertical position and positioning means connected to said support for selectively moving said device.

2. The apparatus according to claim 1 wherein there are 4 first links and 4 second links and said first links are upper links and said second links are lower links.

3. The apparatus according to claim 2 wherein the pivot axes of each of said upper and lower links are spaced the same distance apart.

4. The apparatus according to claim 1 wherein said torsion means includes a coil spring urging a second link upwardly and a coil spring urging a first link downwardly.

5. The apparatus according to claim 4 wherein said torsion means urges interconnected first and second links.

6. The apparatus according to claim 1 wherein a shaft extends along each common pivot axis.

7. The apparatus according to claim 1 wherein a shaft extends along a pivot axis of each interconnected first and second link and one of said members is axially slideable along said shaft to provide an additional direction of horizontal adjustment.

8. The apparatus according to claim 1 wherein the device is an ophthalmic instrument.

9. The apparatus according to claim 7 wherein the device is an ophthalmic instrument and further includes shift means for moving said instrument alternately between two positions spaced along said shafts.

10. The apparatus according to claim 9 wherein said shift means is carried by said device and is connected to said positioning means to enable adjustment of said device in each of the two positions.

* * * * *